US00PP20555P2

(12) United States Plant Patent
Pan

(10) Patent No.: US PP20,555 P2
(45) Date of Patent: Dec. 15, 2009

(54) ***LANTANA* PLANT NAMED 'BANT PIN09'**

(50) Latin Name: *Lantana camara L.*
Varietal Denomination: Bant Pin09

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/291,088

(22) Filed: Nov. 6, 2008

(51) Int. Cl.
*A01H 5/00* (2006.01)

(52) U.S. Cl. ..... Plt./227
(58) Field of Classification Search ..... Plt./227

See application file for complete search history.

*Primary Examiner*—Annette H Para

(74) *Attorney, Agent, or Firm*—S. Matthew Edwards

(57) ABSTRACT

A new *Lantana* plant named 'Bant Pin09,' particularly distinguished by the purple/pink flower color, larger flowers, good floriferiousness, a relatively compact and mounding habit that is well branched, and has dark-green foliage.

1 Drawing Sheet

Latin name of the genus and species of the plant claimed: *Lantana camara L.*

Varietal denomination: 'Bant Pin09'.

BACKGROUND OF THE NEW PLANT

The present invention comprises a new *Lantana,* botanically known as *Lantana camara L.* and hereinafter referred to by the variety name 'Bant Pin09.'

'Bant Pin09' is a product of a planned breeding program. The new cultivar 'Bant Pin09' has purple/pink flowers, larger flowers, good floriferiousness, a relatively compact and mounding habit that is well branched, and has dark-green foliage.

'Bant Pin09' originated from a hybridization in a controlled breeding program in Gilroy, Calif. USA. The female parent was an unpatented hybrid seedling identified as '5-1' with pink color. '5-1' has a shorter plant habit, darker flower color, and fewer basal branches than 'Bant Pin09.'

The male parent of 'Bant Pin09' was an unpatented hybrid seedling identified as '44-1' with a pink color and medium spreading habit. '44-1' is later to flower and has lighter foliage than 'Bant Pin09.'

'Bant Pin09' was selected as one flowering plant within the progeny of the stated cross in May 2005 in a controlled environment in Gilroy, Calif. USA. The pollination took place in July 2004 and the seed sowing in November 2004.

The first act of asexual reproduction of 'Bant Pin09' was accomplished when vegetative cuttings taken from the initial selection in May 2005 in a controlled environment in Gilroy, Calif. USA.

Horticultural examination of plants grown from cuttings of the plant initiated in May 2005 in Gilroy, Calif. USA, and continuing thereafter, has demonstrated that the combination of characteristics as herein disclosed for 'Bant Pin09' are firmly fixed and are retained through successive generations of asexual reproduction.

'Bant Pin09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Bant Pin09' has not been made publicly available more than one year prior to the filing of this application.

DESCRIPTION OF THE DRAWINGS

The accompanying photographic drawing shows typical flower and foliage characteristics of 'Bant Pin09' with colors being as true as possible with an illustration of this type. The photographic drawing shows a flowering potted plant of the new variety and a close-up of the flowers. The photographs were taken in Gilroy, Calif. USA. Both were grown in Gilroy, Calif. USA and were approximately 4 months old.

DETAILED BOTANICAL DESCRIPTION

The measurements were taken in Gilroy, Calif., in April 2008 on plants that were growing in 4 inch pots in a trial setting. Culture of these plants started in January 2008 in a greenhouse. The plants were approximately 4 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. The following traits have been repeatedly observed and are determined to be basic characteristics of the new variety. The combination of these characteristics distinguishes this *Lantana* as a new and distinct variety.

TABLE 1

DIFFERENCES BETWEEN THE NEW VARIETY 'BANT PIN09' AND A SIMILAR VARIETY

| | 'Bant Pin09' | 'Bante Pinka07' |
|---|---|---|
| Flower color | More lavender tone | Less lavender/darker pink |

TABLE 1-continued

DIFFERENCES BETWEEN THE NEW VARIETY 'BANT PIN09' AND A SIMILAR VARIETY

| | 'Bant Pin09' | 'Bante Pinka07' |
|---|---|---|
| Plant habit | Somewhat more compact | Less compact |
| Flowering response | Earlier by 3-5 days | Later to flower |

Plant:

*Form, growth and habit.*—Relatively compact and mounding habit, well branched; apical pinching enhances the number of branches and results in a tighter plant habit.

*Plant height.*—16–21 cm.

*Plant height (inflorescence included).*—23–26 cm.

*Plant width.*—35–40 cm.

Foliage:

*Type.*—Opposite.

*Immature, leaf color, upper surface.*—Closest to RHS 147A.

*Lower surface.*—RHS 147B.

*Mature, leaf color, upper surface.*—Darker than RHS 147A.

*Lower surface.*—RHS 147B.

*Length.*—5.2–6.7 cm.

*Width.*—4.1–5.3 cm.

*Shape.*—Ovate.

*Base shape.*—Attenuate.

*Apex shape.*—Acute.

*Margin.*—Serrate.

*Texture, upper surface.*—Hirsute.

*Texture, lower surface.*—Hirsute; mainly on the veins; glandular hairs.

*Color of veins, upper surface.*—Both surfaces; RHS 144A basally, otherwise indistinct.

*Petioles color.*—RHS 144A.

*Petioles length.*—0.7–0.8 cm.

*Diameter of petioles.*—0.2 cm.

*Texture.*—Both surfaces, hirsute; glandular hairs.

Stem:

*Color of stem.*—RHS 144A; no anthocyanins.

*Length of stem.*—20–25 cm.

*Diameter.*—0.3–0.4 cm.

*Length of internodes.*—2.5–4.0 cm.

*Texture.*—Hirsute; glandular hairs.

Inflorescence:

*Type.*—Umbel like; flattened semi-sphere, the florets are sessile on an ovate receptacle.

*Blooming habit.*—Flowers continuously from spring through fall.

*Number of open flowers per inflorescence.*—40–45.

*Quantity of inflorescences per plant.*—30–40.

*Lastingness of individual blooms on the plant.*—About 4 weeks depending on temperatures.

*Fragrance.*—Slightly spicy.

*Umbel horizontal diameter.*—4.5–5.0 cm.

*Umbel vertical height.*—1.5–2.5 cm.

*Peduncle color.*—RHS 144A, no anthocyanins.

*Length of peduncle.*—2.5–5.0 cm.

*Peduncle diameter.*—0.15–0.2 cm.

*Texture.*—Hirsute; glandular hairs.

Corolla:

*Floret form.*—Salver-shaped to shallow cup-shaped and zygomorphic, with a relatively long tube at the base. Each floret subtended by single bract.

*Floret horizontal diameter.*—1.1–1.3 cm.

*Floret depth.*—2.3–2.5 cm.

*Immature, color of petals, upper surface.*—RHS 4B; RHS 14B at the corolla opening.

*Lower surface.*—RHS 13D; some petals flushed RHS 39C.

*Mature, color of petals, upper surface.*—RHS 75C base color, overlaid with RHS 75A in slight striations; RHS 25B at the corolla opening, overlaid with RHS 25A. Maturing to RHS 75A base color, overlaid with N74C; RHS 25A at the corolla opening.

*Lower surface.*—RHS 75C and RHS 155B basally. Maturing to RHS 75C with a bit of RHS N74B at the margins and RHS N155B basally.

*Petal length.*—0.5–0.6 cm.

*Petal diameter.*—0.5–0.9 cm.

*Apex.*—Mucronulate.

*Margin.*—Entire.

*Shape.*—Obovate.

*Degree of lobation.*—Moderate.

*Texture, upper surface.*—Papillose.

*Texture, lower surface.*—Slightly hirsute.

*Corolla tube, color, outer surface.*—Closest to and between RHS 51A and B.

*Corolla tube, color, inner surface.*—RHS N155B.

*Corolla tube length.*—1.2–1.5 cm.

*Diameter (at opening).*—0.1–0.15 cm.

*Corolla tube texture, outer surface.*—Hirsute.

*Corolla tube texture, inner surface.*—Hirsute.

Bud (just before opening):

*Color.*—RHS 26D overlaid slightly with RHS 33D.

*Length.*—1.0–1.2 cm.

*Width.*—0.4 cm at the tip.

*Shape.*—Tubular.

Bract:

*Color.*—RHS 144C.

*Length.*—0.2 cm.

*Diameter.*—0.1 cm.

*Texture.*—Hirsute on the outer surface; glandular hairs on the inner surface.

Calyx:

*Number of sepals.*—5, fused sepals forming a short tube around the base of each floret.

*Color of sepals.*—RHS 147B both surfaces.

*Length of sepals.*—0.5–0.8 cm.

*Width of sepals.*—0.1–0.15 cm.

*Apex shape.*—Obtuse.

*Apex margins.*—Shallowly fringed.

*Texture, upper surface.*—Hirsute; glandular hairs.

*Texture, lower surface (inside).*—Glabrous.

Reproductive organs:

*Pistil.*—1.

*Length.*—0.6 cm.

*Style color.*—RHS 155A.

*Style length.*—0.4 cm.

*Stigma color.*—RHS 1C.

*Stamens.*—4.

*Color of filaments.*—RHS 155B.

*Length of filaments.*—0.5 cm.

*Anther color.*—RHS 199C.

*Length of anthers.*—0.1 cm.

*Anther shape.*—Ovate.

*Pollen amount.*—Sparse.

*Color of pollen.*—RHS 10B.

*Fertility/seed set.*—This hybrid sets a sparse amount of seed and those seeds have not been observed for characteristics.

Disease/pest resistance: Disease resistance or susceptibility has not been observed on this hybrid.

What is claimed is:

1. A new and distinct variety of *Lantana* plant named 'Bant Pin09,' substantially as illustrated and described herein.

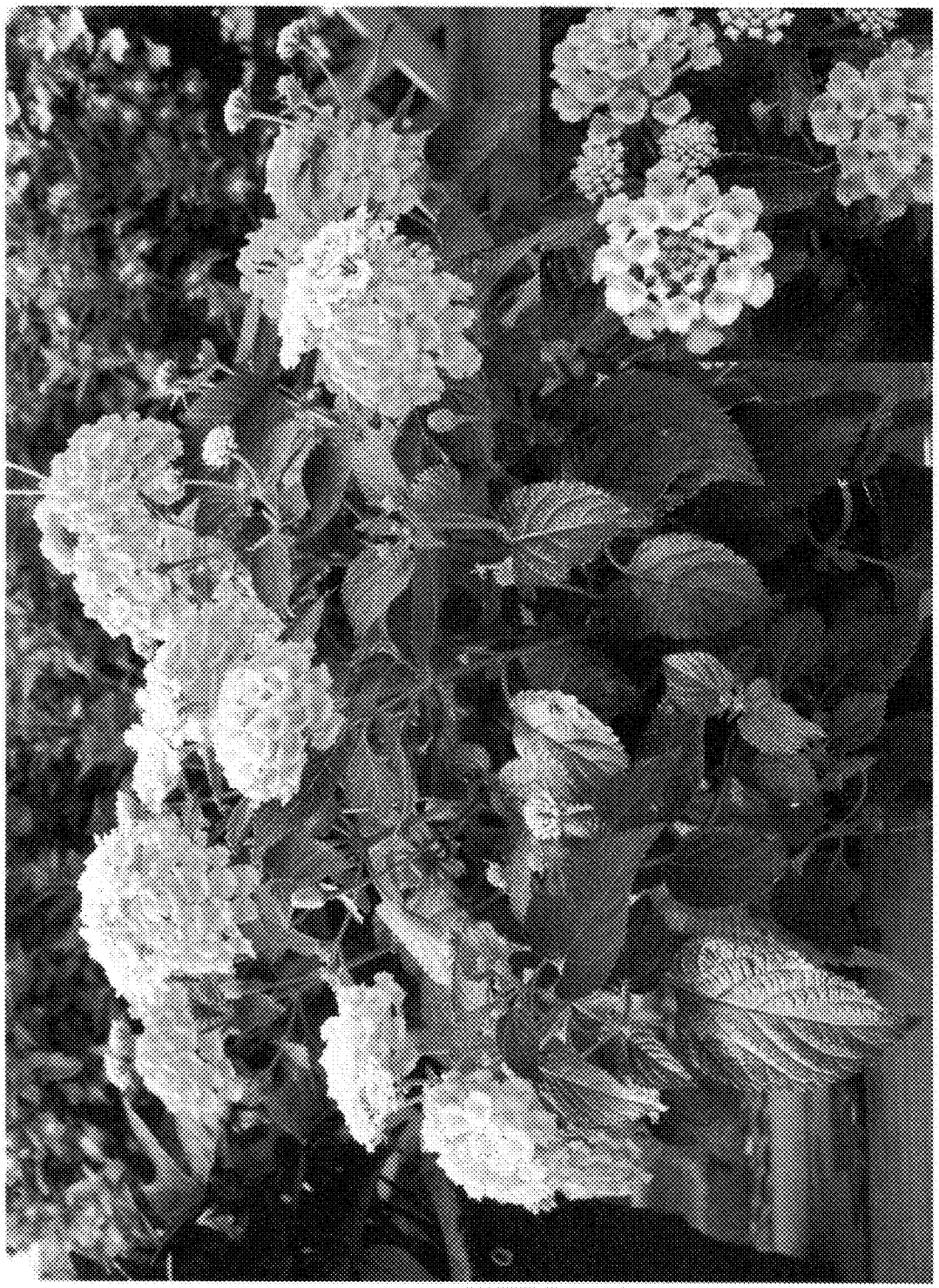

* * * * *